US006961607B2

(12) United States Patent
Uzgiris

(10) Patent No.: US 6,961,607 B2
(45) Date of Patent: Nov. 1, 2005

(54) METHOD FOR ASSESSING MYOCARDIAL ANGIOGENESIS

(76) Inventor: Egidijus E. Uzgiris, 1206 Viewmont Dr., Niskayuna, NY (US) 12309

( * ) Notice: Subject to any disclaimer, the term of this patent is extended or adjusted under 35 U.S.C. 154(b) by 372 days.

(21) Appl. No.: 10/209,989

(22) Filed: Jul. 31, 2002

(65) Prior Publication Data
US 2004/0024318 A1 Feb. 5, 2004

(51) Int. Cl.[7] .......................... A61B 5/05; A61B 5/055
(52) U.S. Cl. ........................ 600/420; 424/9.3
(58) Field of Search ............................ 600/420, 410, 600/407, 431; 250/302, 303; 424/9.3, 9.31, 424/9.32, 9.4

(56) References Cited

U.S. PATENT DOCUMENTS

| | | | |
|---|---|---|---|
| 4,431,968 A | 2/1984 | Edelstein et al. | |
| 4,665,365 A | 5/1987 | Glover et al. | |
| 5,362,475 A | 11/1994 | Gries et al. | |
| 5,554,748 A | 9/1996 | Sieving et al. | |
| 5,762,909 A | 6/1998 | Uzgiris | |
| 6,121,775 A | 9/2000 | Pearlman | |
| 6,235,264 B1 | 5/2001 | Uzgiris | |
| 6,322,770 B1 * | 11/2001 | Rajopadhye et al. | 424/1.65 |
| 6,511,648 B2 * | 1/2003 | Harris et al. | 424/1.65 |
| 6,511,649 B1 * | 1/2003 | Harris et al. | 424/1.69 |
| 6,524,553 B1 * | 2/2003 | Harris | 424/9.34 |
| 6,683,163 B2 * | 1/2004 | Harris et al. | 534/15 |
| 2001/0028876 A1 | 10/2001 | Uzgiris et al. | |
| 2001/0028877 A1 | 10/2001 | Uzgiris | |

FOREIGN PATENT DOCUMENTS

| | | |
|---|---|---|
| WO | 92/07259 | 4/1992 |
| WO | WO 01/89584 | 11/2001 |

OTHER PUBLICATIONS

Sieving et al. "Preparation and Characterization of Paramagnetic Polychelates and Their Protein Conjugates" Bioconjugate Chem., 1.65-71 (1990).
Brooks, P.C. et al. Science, 264,569-571 (1994).
Sipkins, D.A. et al. Nature New Medicine, 4,623-626 (1998).
Kahler et al., Quantitative Regional Blood Volume Studies in Rat Myocardium in Vivo, Physikalisches Institut, Germany 1998.
Ogan et al., Albumin Labeled with Gd-DTPA—An Intravascular Contrast Enhancing Agent for Magnetic Rsonance Blood Pool Imaging: Preparation and Characterization, 1987.

* cited by examiner

*Primary Examiner*—Daniel Robinson
(74) *Attorney, Agent, or Firm*—Carter, DeLuca, Farrell & Schmidt, LLP.

(57) ABSTRACT

Polymeric contrast agents are used to monitor myocardial neovascularization. The agent is injected and images of the myocardium are obtained at various time intervals after injection. Localized image enhancement indicates an area of increased angiogenesis.

23 Claims, 4 Drawing Sheets

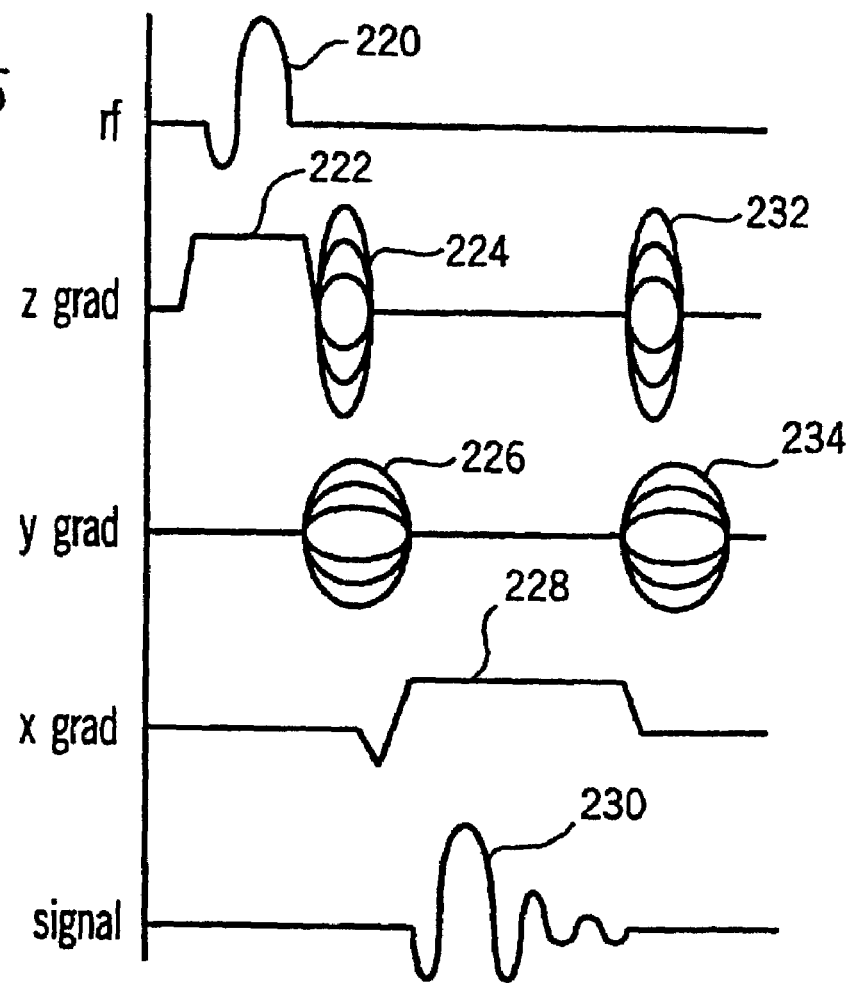

METHOD FOR ASSESSING MYOCARDIAL ANGIOGENESIS

BACKGROUND

1. Technical Field

This disclosure relates to methods for assessing myocardial angiogenesis using contrast agents and imaging techniques, such as, for example, magnetic resonance imaging (MRI).

2. Background of Related Art

Angiogenesis (also known as neovascularization) in mature adult tissues is a tightly regulated process that can occur in a number physiological and pathophysiological conditions. In particular, myocardial collateral vessels in coronary circulation can develop in response to progressive coronary artery occlusion. These coronary collaterals are natural bypass vessels that can develop in the ischemic areas of the heart to provide an alternate route for nutrient blood supply. Typical myocardial collaterals are small thin-walled vessels, ranging from about forty to about two hundred micrometers in diameter, and their presence is an indication of advanced coronary disease. Although coronary collaterals are not detected in all patients with advanced coronary disease, their presence is associated with smaller infarcts and a more benign clinical course. Sufficient collateralization can prevent the damage of heart attack. For this reason, identification of collateral circulation is clinically important. Despite its value, identification of collateralized tissue has to date been quite limited due to the insensitivity of presently available detection techniques.

Clinical agents that are currently in use detect blood capillaries. However, these agents leak out of the vasculature rapidly and have no special signal associated with newly sprouting capillaries induced by angiogenesis. Thus, the monitoring of capillary number and condition is both complex and prone to error using the presently available agents.

The difference between new and normal capillaries is further masked by the fact that the presently used clinical agent freely crosses most normal endothelium as well as new angiogenic endothelium. The monitoring of therapy to revive damaged myocardium must be sensitive to the induction of new blood vessels so that the efficacy of the therapy can be closely monitored and if necessary the therapy can be altered quickly to be more efficacious.

Therefore, it would be advantageous to be able to generate a more specific signal related to the growth of new endothelium to correctly monitor the course of therapy and reduce delay in the adjustment of the course of treatment.

SUMMARY

Polymeric contrast agents are used in accordance with this disclosure monitor myocardial angiogenesis. The agent is injected and an MR signal of the myocardium is recorded at various time intervals after injection.

Suitable polymeric contrast agents include a paramagnetic entity complexed with a substituted polymeric carrier molecule. The preferred substituted polymeric carriers have a length 5 to 500 times greater than their diameter, a net negative charge, and form a worm-like chain conformation with a long persistence length. In particularly useful embodiments, lanthanide complexes (e.g., gadoliniumdiethylenetriamine pentaacetic acid complexes) are attached to the polymer backbone to create complex molecules which are introduced into a blood vessel of the subject.

These polymeric contrast agent molecules do not pass through normal capillary walls. The polymeric contrast agents penetrate the walls of new angiogenic blood vessels, however, due to their increased permeability and collect in the interstitial space. Thus, strong signals are associated with the newly formed blood vessels after a period of time. Penetration of the blood vessel wall is enhanced by the worm-like configuration of the polymeric contrast agent molecule which allows the molecule to "snake" around fixed obstacles and pass through the capillary wall by a mechanism of polymer reptation.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawing, in which:

FIG. 5 is a graphic representation of a pulse sequence performed by the MRI system of FIG. 4 to practice an embodiment of the methods described herein.

DETAILED DESCRIPTION OF PREFERRED EMBODIMENTS

Figure 1:
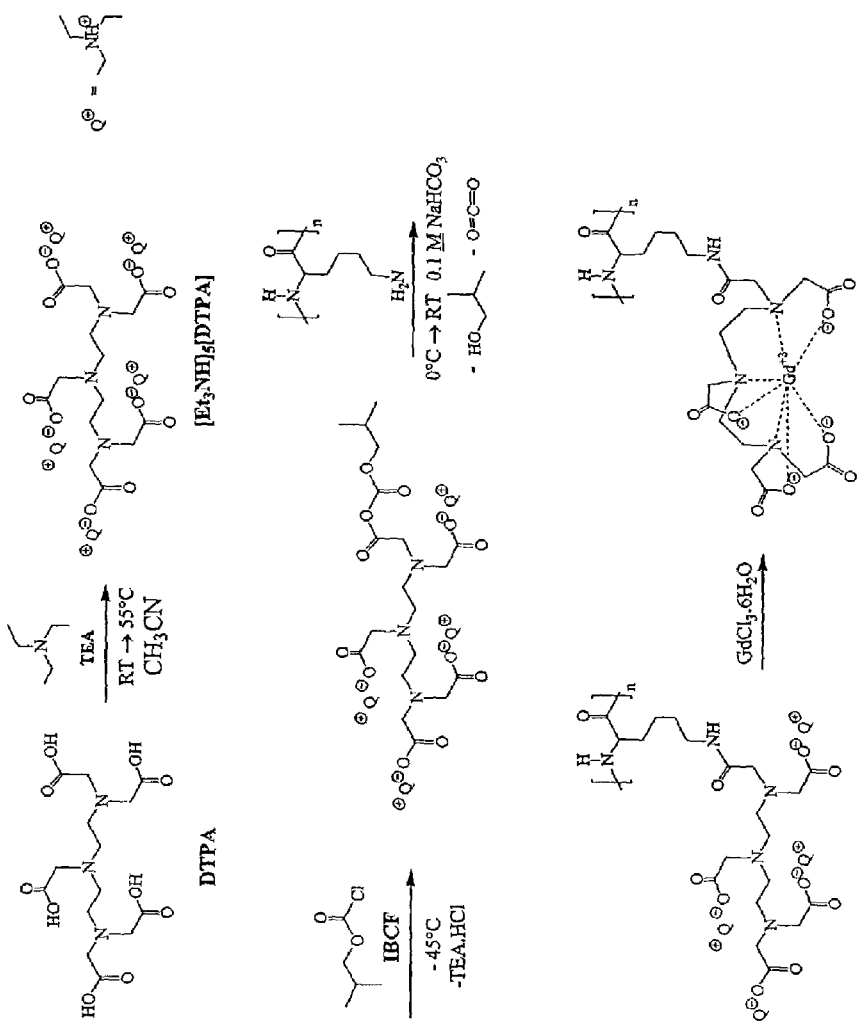
FIG. 1 is a reaction scheme for preparing highly conjugated polymers in accordance with one embodiment of this disclosure.

Methods for sensitive measurements of the growth of new blood vessels in the myocardium are accomplished in accordance with this disclosure by administering a polymeric contrast agent to a subject and obtaining at least two images of the heart. The use of polymeric contrast agents and imaging techniques allows for rapid imaging and hence rapid feedback on a course of treatment being administered to treat myocardial angiogenesis.

Suitable polymeric contrast agents include a paramagnetic entity complexed with a substituted polypeptide carrier molecule. The polymeric contrast agents have a length that is 5 to 500 times greater than their diameter, a net negative charge, and form a worm-like chain conformation with a long persistence length The worm-like configuration of the complex molecule is achieved by attaching a sufficient number of steric hindrance molecules along the polypeptide chain to eliminate or reduce intra-chain ionic bonds as well as to allow charge repulsion between chelating moieties to unfold and extend the polymer chain. The amount of substitutions (also referred to as the degree of conjugation) thus affects the configuration of the resulting complex, with a higher degree of conjugation providing a more consistent extended structure and better diagnosis. A degree of conjugation of above 90% is typically required for the proper polymer configuration to be realized in the case of a carrier molecule having a lysine homopolymer backbone. Lower degrees of conjugation can be tolerated for certain carrier molecules having an amino acid copolymer backbone, such as, for example, a backbone that is a copolymer containing lysine and either glutamic or aspartic acid.

The present carrier molecules include a polymer backbone that is substituted with steric hindrance molecules which facilitate the attachment of a paramagnetic entity and which, due to their physical size, provide a physical restraint on polymer bending.

The nature of the polymer backbone is not critical, provided that the polymer has pendant groups which can be reacted with an activated steric hindrance molecule ("SHM") as described below to provide a polymer-SHM copolymer having an elongated structure. Suitable pendant groups which may be present ion the polymer include, but are not limited to amine groups, carboxyl groups and hydroxyl groups. Useful polymers include homo- and co-polymers of poly(amino acids), poly(vinyl amine), poly(4-aminostyrene), poly(acrylic acid), poly(methacrylic acid), poly(carboxynorbomene), and dextran. Preferably, the polymer is a polypeptide. The polypeptide can be an amino acid homopolymer or a copolymer of two or more amino acids. Preferably, the polypeptide is selected from the group consisting of polylysine, polyglutamic acid, polyaspartic acid, copolymers of lysine and either glutamic acid or aspartic acid. Other polymers may be used provided that after reaction with the SHM, the resulting copolymer has an elongated structure characterized by a molecular length that is 5 to 500 times the cross-sectional diameter of the copolymer molecule and a net negative charge in an aqueous environment. In addition, the polymer preferably is of sufficient length to increase the time in which the product circulates in the blood. For polypeptides, the polymer backbone can advantageously be from 35 to 1500 amino acid residues long. Because the polymeric backbone is synthetic, the length can be tailored to provide desired residence times in the body. Clearance from the blood is rapid for short molecules, resulting in a short plasma lifetime. Plasma lifetime increases rapidly as the polymers increase in length. For example, where the polymer is a polypeptide, a plateau is reached for a molecular length of about 500 residues and little further change in lifetime occurs. Not only does the use of a synthetic polypeptide provide the ability to modify the polymer length so as to change the blood circulation times to smaller values, but the ability to modify the polymer length to probe small permeability modulations is also provided.

A preferred homopolymer is a lysine homopolymer.

Where a copolymer forms the backbone of the carrier molecule, the copolymer preferably contains lysine units and either glutamic acid units, aspartic acid units, or both. Glutamic and/or aspartic acid units may constitute from about 20 to about 60 percent of the copolymer. Preferably, the copolymer is a glutamic acid-lysine copolymer. Particularly useful copolymers have glu:lys ratios of about 1:4 for long (>400 residue) polymer constructs and ratios of about 6:4 for short (<200 residue) polymer constructs. A high content of lysine is believed advantageous for imaging as it allows a high loading of the copolymer with paramagnetic ions. Without wishing to be bound by any theory, it is believed that the presence of glutamic acid residues in the copolymer backbone accomplishes two things. First, it is believed that the glutamic acid residues provide a stiffer initial copolymer backbone for the synthesis of the complete construct. Second, it is believed that the presence of glutamic acid residues in the copolymer promotes extension of the final polymer through charge repulsion.

At least a portion of the polymer backbone have steric hindrance molecules substituted thereon. The steric hindrance molecule ("SHM") can be any molecule that by its physical size enforces an elongated conformation by providing steric hindrance between neighboring steric hindrance molecules. Preferably the SHM is neutral in charge or presents negative charges in an aqueous environment along the polymer chain to assist in keeping the polymer backbone straight through Coulombic repulsion.

In particularly useful embodiments, the SHM contains or chelates an imaging producing entity. Suitable imaging producing entities include paramagnetic entities, entities which undergo nuclear reaction resulting in release of detectable radiation. Non-limiting examples include ions which release alpha particles, gamma particles, beta particles, or positrons. Such image producing entities are known to those skilled in the art. Gamma emitters include, for example, $^{111}$In and $^{153}$Gd. Positron emitters include, for example, $^{89}$Zr, which may be employed in positron emission tomography (PET) imaging.

Particularly preferred steric hindrance molecules are molecules that chelate with paramagnetic entities. As those skilled in the art will appreciate, paramagnetic entities include certain transition metals and lanthanide ions. Any molecule known to complex with paramagnetic entities and which is of sufficient size to provide steric hindrance against polymer bending can be used as the SHM. Preferably, the SHM has a net negative charge. Suitable lanthanide ion chelating molecules include, but are not limited to diethylenetriaminepentaacetic acid (DTPA), 1,4,7,10-Tetraazacyclododecane-1,4,7,10-tetraacetic acid (DOTA), 1,4,7,10-Tetraazacyclododecane-1,4,7,10-tetrakis(2-propionic acid) (DOTMA), 1,4,8,11-Tetraazacyclotetradecane-1,4,8,11-tetraacetic acid (TETA), 1,4,7,10-Tetraazacyclododecane-1,4,7,10-tetrakis[3-(4-carboxyl)-butanoic acid], 1,4,7,10-Tetraazacyclododecane-1,4,7,10-tetrakis(acetic acid-methyl amide), 1,4,7,10-Tetraazacyclododecane, 1,4,7,10-tetrakis (methylene phosphonic acid), and p-Isothiocyanatobenzyl-1,4,7,10-tetraazacyclododecane-1,4,7,10-tetraacetic acid (p-SCN-Bz-DOTA). Ligands useful for chelating for other ions (such as, for example, Fe(III), Mn(II), Cu(II), etc.) include Bis(thiosemicarbazone) and derivatives, Porphyrins and derivatives, 2,3-Bis(2-thioacetamido)propionates and derivatives, N,N'-bis(mercaptoacetyl)-2,3-diaminopropanoate, and Bis(aminoethanethiol) and derivatives.

To attach the SHM to the polymer, an activating group is provided on the SHM. The activating group present on the SHM can be any group which will react with a polymer. Suitable groups include, but are not limited to mixed carbonate carbonic anhydride groups, succinimidyl groups, amine groups and dicyclohexylcarbodiimide (DCC) groups. Those skilled in the art will readily envision reaction schemes for providing an activating group on any given SHM.

In one embodiment, the SHM is DTPA and the activating groups are mixed carbonate carbonic anhydride groups. In particularly useful embodiments, a substantially mono-activated SHM is provided. The term "activated" means that a functional group is present on the molecule which permits covalent bonding of the molecule to appropriate amino acids. By the term "substantially mono-activated" it is meant that about 90% or more of the steric hindrance molecules contain only a single activated site. Mono-activation is believed to more consistently result in high levels of conjugation. A typical reaction scheme for activating DTPA and reacting it with a polypeptide backbone is shown in FIG. 1. As seen therein, a monoanhydride-DTPA is first prepared. Specifically, a flask is charged with acetonitrile and DTPA. Triethylamine is then added via syringe. The solution is warmed to 60° C. under a nitrogen atmosphere. The mixture is stirred until homogeneous. The clear solution is then cooled to −45° C. under nitrogen atmosphere and isobutyl chloroformate is slowly added to result in the mono-anhydride of DTPA. As those skilled in the art will appreciate, DTPA has five acid groups available for conversion to anhydride. However, since substantially mono-activated DTPA is desired, only one of these acid sites should be converted to anhydride. It has unexpectedly been found that the slow addition of the chloroformate while cooling below −40° C. accomplishes this result, i.e., that about 90% or more of the DTPA is a monoanhydride of DTPA.

The activated SHM is then reacted with the polymer backbone. The precise conditions for reacting the polymer with the activated SHM will depend upon a number of factors including the particular polymer chosen and the specific SHM used. Those skilled in the art will readily envision reaction schemes for any given pair of materials to produce the desired substituted polymer product.

In a particularly useful embodiment, for example, the monoanhydride-DTPA described above is simply added dropwise to an aqueous solution of polylysine under ambient atmospheric conditions.

In another example, where the reactive pendant groups on the polymer backbone are electrophilic groups (such as, for example, a carboxylic acid groups), the anhydride of DTPA described above can be reacted overnight with a diamine (in which the diamine is in large excess to the anhydride). Ethylene diamine is a suitable choice, giving in the end a DTPA linkage of the desired length to achieve proper steric hindrance against polymer chain bending. The product is separated from the diamine and from DTPA which was not reacted, by ion exchange chromatography. The product is substantially mono-amine DTPA. Where the substantially mono-activated steric hindrance molecule is the foregoing monoamine-DTPA, it can be linked to a carboxyl group containing polymer (such as, for example, poly-glutamic acid) by a carboxyl coupling method. The carboxy acid groups of the polymer are activated by a coupling reagent, such as, for example, 1 Ethyl-3-(3-Dimethylaminopropyl) carbodiimide Hydrochloride (EDC) (Pierce, Rockford, Ill.). The activated carboxy acid groups on the polymer are then combined with the monoamine-DTPA to produce an amide linkage of the DTPA to the polymer backbone as a sidechain which acts as a steric hindrance straightening the polymer backbone.

The resulting polymer-steric hindrance molecule copolymer is then purified. During purification, the polymer-SHM copolymer is separated from the volatile solvents and other impurities. Any known techniques can be used to purify the polymer-SHM copolymers.

In a particularly useful embodiment, where a polypeptide backbone is used, a purification scheme is employed which does not result in complete drying of the polymer-SHM copolymer. It has unexpectedly been determined that excessive dryness affects the configuration of the copolymer and interferes with the determination of degree of conjugation.

A preferred purification scheme involves first exposing the reaction mixture to reduced pressure to remove impurities that are more volatile than water. Care should be taken not to remove all water from the reaction mixture during this step. The next step in this preferred purification scheme is to centrifuge the remaining reaction mixture. Soluble impurities remain in the supernatant fluid. The retentate from the centrifuge step is resuspended and subjected to dialysis. Optionally, ultrafiltration is performed on the dialyzed polymer. Techniques for these processes are within the purview of those skilled in the art.

The resulting product can then be characterized using any technique known to those skilled in the art, such as, for example, high performance liquid chromatography (HPLC).

Once the polymer-SHM copolymer is obtained, an image producing entity is incorporated into the conjugated polymer. Thus, for example, to achieve a MR active agent, a paramagnetic ion (such as, for example, gadolinium) can be incorporated into the product polymer chelating DTPA groups by dropwise addition of a solution containing an gadolinium salt such as, for example, gadolinium chloride or gadolinium citrate. The dropwise addition of Gd continues until a slight indication of free Gd (not chelated by available DTPA groups) is noted (small aliquots of polymer solution added to 10 microMolar of arzenzo IIII in acetate buffer—free Gd turns the dye solution blue). The Gd-loaded highly conjugated polymer is then ready for introduction into a blood vessel of the subject.

In certain embodiments, the conjugated polymer can also be used for delivery of a therapeutic agent. It is also contemplated that a therapeutic agent can be attached at a few sites along the substituted polymer chain. The therapeutic entity can be attached to the conjugated polymer using techniques known to those skilled in the art. It is also contemplated that, the polymer backbone can be highly conjugated with a non-therapeutic SHM which chelates an imaging agent and a therapeutic agent can be bound to the SHM at a few sites along the substituted polymer chain, rather than being bound directly to the polymer backbone.

In the event that the pores of the angiogenic blood vessels are not simple channels, a process called reptation allows elongated worm-like molecules to wiggle around obstacles, and to pass through restricted openings, that globular or coiled molecules would be unable to pass through.

The present polymeric contrast agent molecules have a cross sectional diameter which is larger than that of the pores of normal blood vessels such that they are contained within the blood vessels in the normal state but have a cross sectional diameter smaller than that of the pores of newly formed vessels produced during angiogenesis such that they may readily pass out of the capillary and into the surrounding tissue. Polymeric contrast agents having a diameter of approximate 20–50 Angstroms (Å) generally pass through pore structures of the new vessels, but not that of normal vessels.

In order to be effective at concentrating outside of angiogenic blood vessels, the polymeric contrast agent molecules also advantageously can have a length long enough to increase the time in which they circulate in the blood, but small enough to pass out of the vessel. Once outside the vessel, longer molecules tend to remain there. In addition, very large macromolecular agents may not provide enough signal due to the changes in capillary permeability, while the small agents presently in clinical use penetrate normal capillaries to begin with so that changes would be more difficult to detect.

An elongated, worm-like conformation of a macromolecule results in greater uptake than other conformations, such as folded, or globular conformations. Conformation may be measured by determining the radius of gyration and persistence length of the molecule. This may be determined by light scattering.

Figure 2:
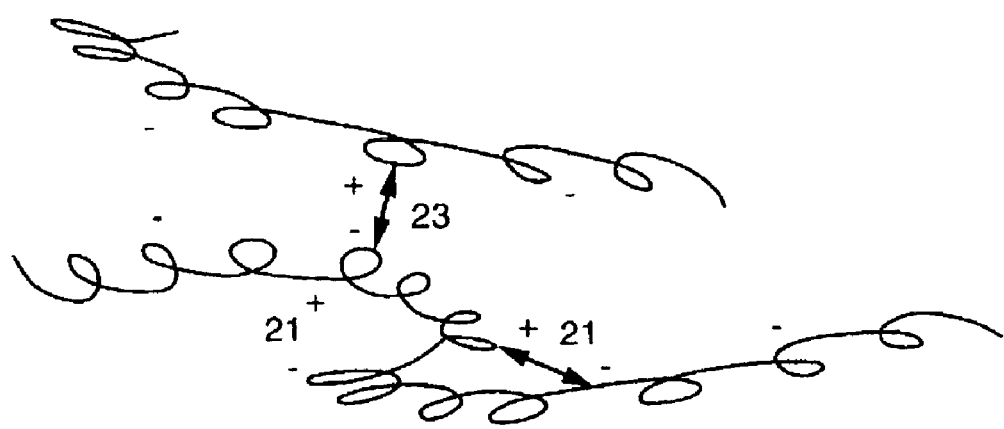
FIG. 2 is an illustration of inter-strand and intra-strand cross-linking of polypeptides.

Conformation is a result of intra-chain charge interaction, and rigidity of the molecule. The polymeric contrast agent molecules are selected to be polypeptides. However, many polypeptides tend to fold into tight random coils due to the relatively free rotation around each peptide bond. Also, if each polypeptide is composed of opposite charge amino acids, then intra-chain charge interaction as shown by bond 21 in FIG. 2. Inter-chain charge interaction between chains may also occur as shown by bond 23 of FIG. 2. If there is significant intra-chain charge interactions, the polymeric contrast agent molecules may assume a globular, or folded, conformation.

The conformation attained by the present polymeric contrast agents is that of a worm-like shape being essentially a stretched out, extended chain with little folding. A measure of the "straightness" of a molecule is a persistence length. Persistence length is related to a radius of gyration, measured by light scattering experiments. A folded polypeptide such as poly-L-lysine (PLL) with little or no substitution, has a low persistence length of about 10 Angstroms (Å), and is not suitable for monitoring angiogenesis. Therefore, the present polymeric contrast agents preferably have a persistence lengths of 100–600 Å.

It is sometimes difficult to measure the persistence length of certain molecules by light scattering to determine their conformation because of the effects of contaminant particles in the test solutions. However, it was found that by measuring the magnetic resonance (MR) $T_1$ relaxation of a paramagnetic entity attached to the carrier, one could infer the conformation of the molecules of interest. This is performed by attaching paramagnetic ions, such as gadolinium, to the chelators along the polymer chain When the carrier molecule is in an elongated conformation, the chelator/MR active entity is free to rotate about its attachment point to the main chain, allowing a long $T_1$ relaxation time of the surrounding water protons which are the source of the MR signal.

When the carrier molecule is in a globular or highly folded conformation, steric hindrance, and molecular crowding causes interaction with the chelator/MR active entity restricting rotation about its bond to the main chain. Thus, the chelator/MR active entity moves only with the general slow motion of the carrier molecule. This produces a short $T_1$ relaxation time.

A high relaxivity is associated with a molecule which folds upon itself into a globular conformation, such as albumen, at about 15 sec.$^{-1}$ milliMolar$^{-1}$ (sec$^{-1}$ mM$^{-1}$). A low relaxivity is associated with an elongated molecule such as highly substituted Gd-DTPA PLL$^h$ in which the Gd can rotate rapidly, having a relaxivity of about 8 sec.$^{-1}$ mM$^{-1}$. The optimum conformation of the present invention is associated with a relaxivity of 7–8 sec.$^{-1}$ mM$^{-1}$. When the relaxivity of a peptide agent was high, the uptake coefficient of such an agent was invariably low, evidently due to the absence of the reptation mechanism.

Since many in-vivo chemical entities have a negative charge, molecules introduced into the subject can advantageously have a net negative charge to reduce agglutination and to allow for stable long circulation in the blood plasma. It is known that negatively charged dextran molecules undergo glomerular filtration at a much slower rate than equivalent dextran molecules of positive charge or neutral charge.

The high net negative charge is also desirable since it also assists in the polymeric contrast agent molecules to retaining their elongated, worm-like conformation.

Figure 3:
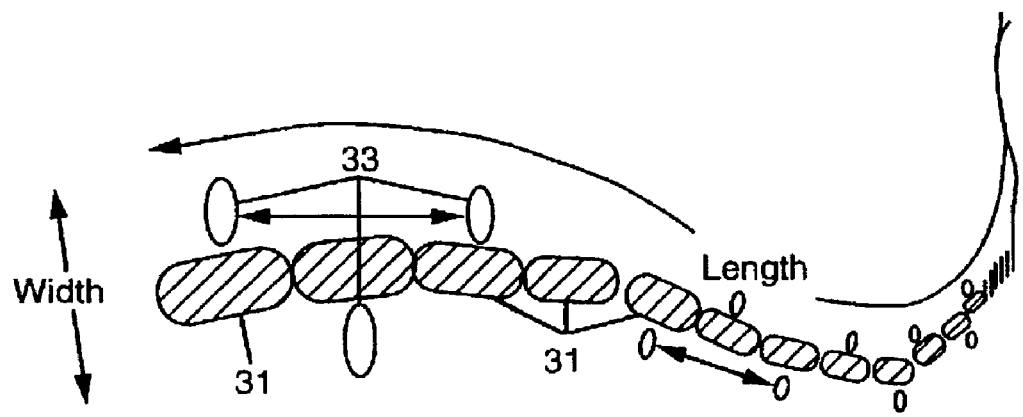
FIG. 3 is an illustration of a highly substituted polypeptide useful as the polymeric contrast agent in the present methods.

In FIG. 3 a polymeric contrast agent having a plurality of side chains substituting the hydrogen atoms is shown. The polymeric contrast agent is comprised of a plurality of amino acids 31, each linked end to end through a polypeptide bond. A plurality of side residues 33 are attached which cause steric hindrances and repulsion to straighten the copolymer chain.

It may be that in some applications, long blood circulation times would be undesirable. The present methods/materials provide the ability to reliably make short polymers of the desired worm-like conformation which allows the possible tailoring of blood circulation time to certain target levels. Blood circulation time is directly dependent on polymer chain length. The response is fast (less than 1 hour) and the clearance from the blood circulation is rapid for shorter polymer lengths, both of which may be desirable in certain clinical procedures.

The polymeric contrast agent molecules used in accordance with certain embodiments of the present disclosure do not normally accumulate in other organs such as muscle, kidney or liver. Therefore, the present agents are particularly well suited for imaging of newly formed, angiogenic blood vessels compared to over other imaging agents that are based on globular proteins or coiled polymers, which tend to show accumulation in liver and kidneys of animal models.

In order to perform one preferred embodiment of the invention, a subject is first imaged and then the polymeric contrast agent is introduced into the subject by injecting the contrast agent intravenously. The dose of the polymeric contrast agent can be in the range of about 0.01 mmoles Gd/Kg to about 0.1 mmoles Gd/Kg. The myocardium is then imaged. Techniques for MR imaging are known and include, for example, the methods disclosed in U.S. Pat. No. 6,121,775. In a particularly useful method, images are obtained beginning immediately after injection and at certain timed intervals. Preferably, the timed intervals are shortly after injection (within 10 minutes) and up to 1 hour post injection. For highest sensitivity of permeability, an image at 24 hours may also be acquired. To determine changes in blood volume, imaging should take place within 10 minutes of contrast agent injection.

Figure 4:
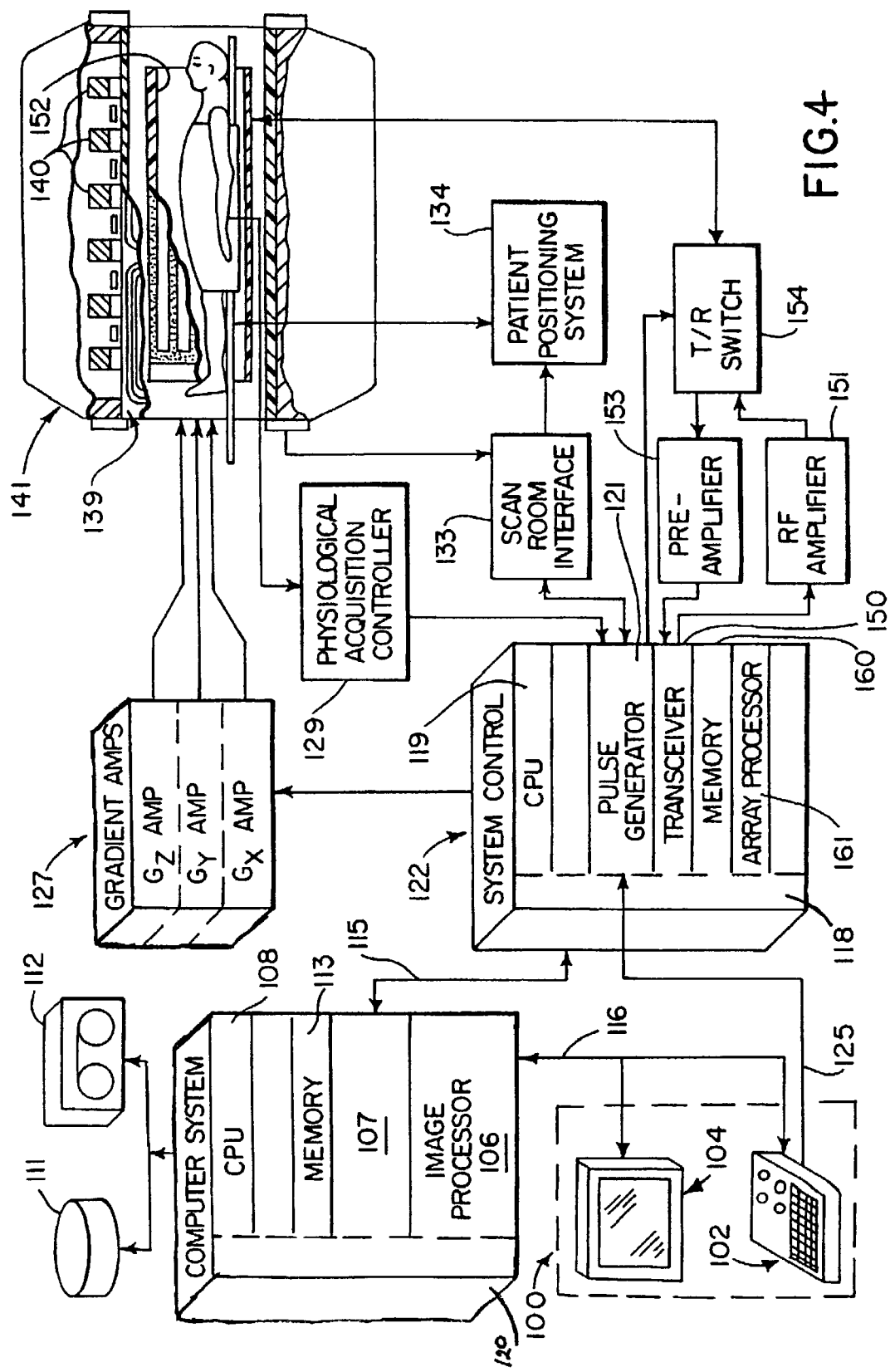
FIG. 4 is a block diagram of an MRI system useful in the performance of the methods described herein.

FIG. 4 shows the major components of a preferred MRI system which can be used in practicing the invention. Operation of the system is controlled from an operator console 100 which includes a keyboard and control panel 102 and a display 104. Console 100 communicates through a link 116 with a separate computer system 107 that enables an operator to control the production and display of images on the screen of display 104. Computer system 107 includes a number of modules which communicate with each other through a backplane 120. These include an image processor module 106, a central processing unit (CPU) module 108 and a memory module 113, known in the art as a frame buffer for storing image data arrays. Computer system 107 is linked to a disk storage 111 and a tape drive 112 for storage of image data and programs, and communicates with a separate system control 122 through a high speed serial link 115.

System control 122 includes a set of modules connected together by a backplane 118. These include a CPU module 119 and a pulse generator module 121 which is coupled to operator console 100 through a serial link 125. Through link 125, system control 122 receives commands from the operator which determine the scan sequence that is to be performed.

Pulse generator module 121 operates the system components to carry out the desired scan sequence, and produces data which determine the timing, strength and shape of the RF pulses to be produced, and the timing and length of the data acquisition window. Pulse generator module 121 is coupled to a set of gradient amplifiers 127, to determine the timing and shape of the gradient pulses to be produced during the scan. Pulse generator module 121 also receives patient data from a physiological acquisition controller 129 that receives signals from a number of different sensors attached to the patient, such as electrocardiogram (ECG) signals from electrodes or respiratory signals from a bellows. Pulse generator module 121 is also coupled to a scan room interface circuit 133 which receives signals from various sensors associated with the condition of the patient and the magnet system. Through scan room interface circuit 133, a patient positioning system 134 receives commands to move the patient to the desired position for the scan.

Gradient amplifier system 127 that receives gradient waveforms from pulse generator module 121 is comprised of $G_x$, $G_y$ and $G_z$ amplifiers. Each gradient amplifier excites a corresponding gradient coil in an assembly 139 to produce the magnetic field gradients used for position encoding acquired signals. Gradient coil assembly 139 forms part of a magnet assembly 141 which includes a polarizing magnet 140 and a whole-body RF coil 152. A transceiver module 150 in system control 122 produces pulses which are amplified by an RF amplifier 151 and coupled to RF coil 152 by a transmit/receive switch 154. The resulting signals radiated by the excited nuclei in the patient may be sensed by the same RF coil 152 and coupled through transmit/receive switch 154 to a preamplifier 153. The amplified NMR signals are demodulated, filtered, and digitized in the receiver section of the transceiver 150. Transmit/receive switch 154 is controlled by a signal from pulse generator module 121 to electrically connect RF amplifier 151 to coil 152 during the transmit mode and to connect preamplifier 153 to coil 152 during the receive mode. Transmit/receive switch 154 also enables a separate RF coil (for example, a head coil or surface coil) to be used in either the transmit or receive mode.

The NMR signals picked up by RF coil 152 are digitized by transceiver module 150 and transferred to a memory module 160 in system control 122. When the scan is completed and an entire array of data has been acquired in memory module 160, an array processor 161 operates to Fourier transform the data into an array of image data. These image data are conveyed through serial link 115 to computer system 107 where they are stored in disk storage 111. In response to commands received from operator console 100, these image data may be archived on tape drive 112, or may be further processed by image processor 106 and conveyed to operator console 100 for presentation on display 104.

The polymeric contrast agent molecules do not penetrate normal blood vessels. Thus if new blood vessels are formed, the neovascularization may be detected by an increase of signal in the tissue being examined over that to be expected from blood volume effects alone in that tissue. Thus, the present methods provide clear direct signals of the quantity of interest-namely, the existence and extent of angiogenesis.

The present methods can be used with a number of different pulse sequences. An exemplary pulse sequence suitable for use in imaging myocardium is gated fast cardiac inversion recovery sequence available with the GE SIGNA scanner sold by the General Electric Company, Milwaukee, Wis. An alternative embodiment employs a fast 3D (three dimensional) RF (radio frequency) phase spoiled gradient recalled echo pulse sequence, depicted in FIG. 5, to acquire the NMR image data. The pulse sequence "3dfgre" available on the General Electric 1.5 Tesla MR scanner sold by General Electric Company, Milwaukee, Wis., under the trademark "SIGNA" with revision level 5.5 system software is used.

As shown in FIG. 5, an RF excitation pulse 220 having a flip angle of from 40° to 60° is produced in the presence of a slab select gradient pulse 222 to produce transverse magnetization in the three-dimensional (3D) volume of interest as taught in Edelstein et al. U.S. Pat. No. 4,431,968 assigned to the instant assignee. This is followed by a slice encoding gradient pulse 224 directed along the z axis and a phase encoding gradient pulse 226 directed along the y axis. A readout gradient pulse 228 directed along the x axis follows, and a partial echo (60%) NMR signal 230 is acquired and digitized as described above. After the acquisition, rewinder gradient pulses 232 and 234 rephase the magnetization before the pulse sequence is repeated as taught in Glover et al. U.S. Pat. No. 4,665,365 assigned to the instant assignee. As is well known in the art, the pulse sequence is repeated and the respective slice and phase encoding gradient pulses 224 and 226 are stepped through a series of values to sample the 3D k-space.

The acquired 3D k-space data set is Fourier transformed along all three axes and a magnitude image is produced in which the brightness of each image pixel indicates the NMR signal strength from each corresponding voxel in the 3D volume of interest.

An initial signal is then compared with the signal enhancement observed at selected times, preferably a short time after injection (within 10 minutes) and then at several time points up to 60 minutes post injection. For highest sensitivity to measure capillary permeability, a subsequent image at about 24 hours may also be taken. The initial image after injection (within 10 minutes) provides a measure of blood volume or microvascular density, for each pixel of the image. Subsequent images then establish the rate of passage of the polymeric contrast agent into the tissue surrounding the blood vessel, again on a pixel by pixel basis. Maps of blood volume and of neovascularization may then be generated and displayed as an image or overlaid on the MR image directly. Both anatomical and physiological features will then be displayed simultaneously, giving radiologists not only the amount of angiogenesis as an average quantity but also its activity as a function of position—a very desirable feature for monitoring the efficacy of myocardial angiogenesis therapy.

Signal enhancements at the endpoint of about 24 hours, that are below some threshold value, preferably about 10% (for the canonical dose of 0.025 mmoles Gd/Kg), signify minimal angiogenic activity. Higher signal values (preferably 75%, most preferably 90%) imply ever increasing angiogenesis. The endpoint signals at 24 hours are due to passage of the polymeric contrast agent through the walls of newly formed blood vessels, as blood concentration levels at that time will be negligibly small for the contrast agents described here, i.e., the reptating polymeric contrast agents.

While specific embodiments of the invention have been illustrated and described herein, it is realized that modifications and changes will occur to those skilled in the art. It is therefore to be understood that the appended claims are intended to cover all such modifications and changes as fall within the true spirit and scope of the invention.

We claim:

1. A method for monitoring myocardial angiogenesis, the method comprising:

intravenously administering a polymeric contrast agent to a subject, the polymeric contrast agent having a conformation with a length that is 5 to 500 times greater than the average diameter of the polymeric contrast agent;

obtaining at least two images of the myocardium of the subject; and comparing the images to assess the growth of new blood vessels, wherein a localized image enhancement indicates an area of increased myocardial angiogenesis.

2. A method as in claim 1 wherein the step of intravenously administering a polymeric contrast agent comprises administering a contrast agent having a polypeptide backbone.

3. A method as in claim 1 wherein the step of intravenously administering a polymeric contrast agent comprises administering a contrast agent having a backbone formed from a polypeptide selected fro the group consisting of polylysine, polyglutamic acid, polyaspartic acid and copolymers of lysine and either glutamic acid or aspartic acid.

4. A method as in claim 1 wherein the step of intravenously administering a polymeric contrast agent comprises administering a contrast agent having a polymer backbone having covalently bound thereto at least one member from the group consisting of diethylenetriaminepentaacetic acid (DTPA), 1,4,7,10-Tetraazacyclododecane-1,4,7,10-tetraacetic acid (DOTA), 1,4,7,10-Tetraazacyclododecane-1,4,7,10-tetrakis(2-propionic acid) (DOTMA), 1,4,8,11 -tetraazacyclotetradecane-1,4,8,11 -tetraacetic acid (TETA), 1,4,7,10-tetraazacyclododecane-1,4,7,10-tetrakis(3-(4-carboxyl)-butanoic acid), 1,4,7,10-tetraazacyclododecane-1,4,7,10-tetrakis(acetic acid-methyl amide), 1,4,7,10-tetraazacyclododecane-1,4,7,10-tetrakis(methylene phosphonic acid), and p-isothiocyanatobenzyl-1,4,7,10-tetraazacyclododecane-1,4,7,10-tetraacetic acid (p-SCN-Bz-DOTA), bis(thiosemicarbazone), derivatives of bis(thiosemicarbazone), porphyrins, derivatives of porphyrins, 2,3-bis(2-thioacetamido)propionates, derivatives of 2,3-bis(2-thioacetamido) propionates, N,N'-bis(mercaptoacetyl)-2,3-diaminopropanoate, bis(aminoethanethiol) and derivatives of bis (aminoethanethiol).

5. A method as in claim 1 wherein the step of intravenously administering a polymeric contrast agent comprises administering a contrast agent at a dose in the range of about 0.01 mmoles Gd/Kg to about 0.1 mmoles Gd/Kg.

6. A method as in claim 1 wherein the step of intravenously administering a polymeric contrast agent comprises administering a contrast agent having a polypeptide backbone having a length of 80 to 1500 amino acid residues.

7. A method as in claim 1 wherein the step of intravenously administering a polymeric contrast agent comprises administering a contrast agent having a diameter in the range of 20 Angstroms to 50 Angstroms.

8. A method as in claim 1 wherein the step of intravenously administering a polymeric contrast agent comprises administering a contrast agent having one or more paramagnetic entities chelated to a polymeric backbone.

9. A method as in claim 1 wherein the step of intravenously administering a polymeric contrast agent comprises administering a contrast agent having one or more gadolinium ions chelated to a polymeric backbone.

10. A method for detecting myocardial angiogenesis, the method comprising:
providing a polymeric contrast agent by reacting a substantially mono-activated steric hindrance molecule with a polymer, to provide a polymer-steric hindrance molecule copolymer having an elongated structure and having a degree of conjugation of 90% or greater and loading the polymer-steric hindrance molecule copolymer with an image producing entity;
intravenously administering the polymeric contrast agent to a subject obtaining at least two images of the myocardium of the subject; and comparing the images to assess the growth of new blood vessels, wherein a localized image enhancement indicates an area of increased myocardial angiogenesis.

11. A method as in claim 10 wherein the step of providing a polymeric contrast agent comprises reacting a substantially mono-activated diethylenetriamine pentaacetic acid with a polypeptide.

12. A method as in claim 10 wherein the step of loading the polymersteric hindrance molecule copolymer with an image producing entity comprises contacting the polymer-steric hindrance molecule copolymer with a solution containing gadolinium ions.

13. A method as in claim 10 wherein the step of intravenously administering the polymeric contrast agent comprises administering the polymeric contrast agent at a dose in the range of about 0.01 mmoles Gd/Kg to about 0.1 mmoles Gd/Kg.

14. A method as in claim 10 wherein the step of intravenously administering the polymeric contrast agent comprises administering a polymeric contrast agent having a diameter in the range of 20 Angstroms to 50 Angstroms.

15. A method for diagnosing coronary disease, the method comprising:
intravenously administering a polymeric contrast agent to a subject having or suspected of having coronary disease, the polymeric contrast agent having a length that is 5 to 500 times its average diameter;
obtaining at least two images of the myocardium of the subject; and
comparing the images to determine the presence of new blood vessels, wherein a localized image enhancement indicates the presence of myocardial angiogenesis and the presence of coronary disease.

16. A method as in claim 15 wherein the step of intravenously administering a polymeric contrast agent comprises administering a contrast agent having a polypeptide backbone.

17. A method as in claim 15 wherein the step of intravenously administering a polymeric contrast agent comprises administering a contrast agent having a backbone formed from a polypeptide selected fro the group consisting of polylysine, polyglutamic acid, polyaspartic acid and copolymers of lysine and either glutamic acid or aspartic acid.

18. A method as in claim 15 wherein the step of intravenously administering a polymeric contrast agent comprises administering a contrast agent having a polymer backbone having covalently bound thereto at least one member from the group consisting of diethylenetriaminepentaacetic acid (DTPA), 1,4,7,10-Tetraazacyclododecane-1,4,7,10-tetraacetic acid (DOTA), 1,4,7,10-Tetraazacyclododecane-1,4,7,10-tetrakis(2-propionic acid) (DOTMA), 1,4,8,11-tetraazacyclotetradecane-1,4,8,11 -tetraacetic acid (TETA), 1,4,7,10-tetraazacyclododecane-1,4,7,10-tetrakis(3-(4-carboxyl)-butanoic acid), 1,4,7,10-tetraazacyclododecane-1,4,7,10-tetrakis(acetic acid-methyl amide), 1,4,7,10-tetraazacyclododecane-1,4,7,10-tetrakis(methylene phosphonic acid), and p-isothiocyanatobenzyl-1,4,7,10-tetraazacyclododecane-1,4,7,10-tetraacetic acid (p-SCN-Bz-DOTA), bis(thiosemicarbazone), derivatives of bis(thiosemicarbazone), porphyrins, derivatives of porphyrins, 2,3-bis(2-thioacetamido)propionates, derivatives of 2,3-bis(2-thioacetamido) propionates, N,N'-bis(mercaptoacetyl)-2,3-diaminopropanoate, bis(aminoethanethiol) and derivatives of bis (aminoethanethiol).

19. A method as in claim 15 wherein the step of intravenously administering a polymeric contrast agent comprises administering a contrast agent at a dose in the range of about 0.01 mmoles Gd/Kg to about 0.1 mmoles Gd/Kg.

20. A method as in claim 15 wherein the step of intravenously administering a polymeric contrast agent comprises administering a contrast agent having a polypeptide backbone having a length of 80 to 1500 amino acid residues.

21. A method as in claim 15 wherein the step of intravenously administering a polymeric contrast agent comprises administering a contrast agent having a diameter in the range of 20 Angstroms to 50 Angstroms.

22. A method as in claim 15 wherein the step of intravenously administering a polymeric contrast agent comprises administering a contrast agent having one or more paramagnetic entities chelated to a polymeric backbone.

23. A method as in claim 15 wherein the step of intravenously administering a polymeric contrast agent comprises administering a contrast agent having one or more gadolinium ions chelated to a polymeric backbone.

* * * * *